United States Patent [19]

Schuler

[11] Patent Number: 5,646,326

[45] Date of Patent: Jul. 8, 1997

[54] ALKYLHYDROGENCHLOROSILANES, PROCESS FOR THEIR PREPARATION AND THEIR USE

[75] Inventor: Joachim Schuler, Marl, Germany

[73] Assignee: Huels Aktiengesellschaft, Marl, Germany

[21] Appl. No.: 561,320

[22] Filed: Nov. 21, 1995

[30] Foreign Application Priority Data

Dec. 1, 1994 [DE] Germany ............................. 44 42 753.0

[51] Int. Cl.$^6$ ........................................................ C07F 7/08
[52] U.S. Cl. ............................. 556/474; 556/487; 556/479
[58] Field of Search ..................................... 556/474, 487, 556/479

[56] References Cited

U.S. PATENT DOCUMENTS

| | | | |
|---|---|---|---|
| 2,406,605 | 8/1946 | Hurd | 556/474 |
| 2,823,218 | 2/1958 | Speier et al. | 556/479 |
| 3,793,358 | 2/1974 | Bauer et al. | |
| 4,115,426 | 9/1978 | Hiiro et al. | |
| 4,181,673 | 1/1980 | Schumann et al. | 556/487 |
| 4,309,558 | 1/1982 | Koga et al. | 556/487 X |
| 5,015,624 | 5/1991 | Schulz | 556/474 |
| 5,329,038 | 7/1994 | Chadwick et al. | 556/474 |

FOREIGN PATENT DOCUMENTS

| | | |
|---|---|---|
| 0348902 | 1/1990 | European Pat. Off. . |
| 1232580 | 1/1967 | Germany . |
| 324091 | 2/1991 | Japan . |

OTHER PUBLICATIONS

Chemical Abstracts, vol. 119, No. 7, AN–72830u, Aug. 16, 1993, G.M. Vereninov, et al., "Synthesis of Hydrogen–Containing Chloro–and Organochlorosilanes".

J. Phys. Chem., vol. 97, pp. 720–728, 1993, Mark D. Allendorf, et al., "Theoretical Study of the Thermochemistry of Molecules in the Si–C–Cl–H System".

Ullmanns Encyklopaedie der Technischen Chemie, vol. 21, pp. 484–511, 1982.

Ullmanns Encyklopaedie der Technischen Chemie, vol. 15, pp. 748,769, 1964.

*Primary Examiner*—Paul F. Shaver
*Attorney, Agent, or Firm*—Oblon, Spivak, McClelland, Maier & Neustadt, P.C.

[57] ABSTRACT

Alkylhydrogenchlorosilanes of formula I $$R_{(4-n-m)}SiCl_nH_m \qquad (I),$$

wherein m and n are each equal to 1 or 2 and m+n≦3 and R is an alkyl group having from 1 to 5 carbon atoms, are prepared by reacting alkylchlorosilanes of formula II $$R_{(4-p)}SiCl_p \qquad (II),$$

wherein p is equal to 1, 2 or 3, with hydrogen.

The alkylhydrogenchlorosilanes are employed as a starting material in hydrosilylation reactions.

16 Claims, No Drawings

ALKYLHYDROGENCHLOROSILANES, PROCESS FOR THEIR PREPARATION AND THEIR USE

BACKGROUND OF THE INVENTION

Field of the Invention

The invention relates to alkylhydrogenchlorosilanes of formula I $$R_{(4-n-m)}SiCl_nH_m \quad (I),$$

where m and n are each equal to 1 or 2 and m+n≦3 and R is an alkyl group having from 1 to 5 carbon atoms, to a process for their preparation and to their use.

DESCRIPTION OF THE BACKGROUND

Alkanyl-, alkenyl- and alkynylchlorosilanes can be prepared by the hydrosilylation of the double or triple bond of the corresponding unsaturated hydrocarbons. Dimethylchlorosilane (DMCS) and methyldichlorosilane (MDCS) find, via the hydrosilylation reaction, wide use in the synthesis of organochlorosilanes.

It is known that (DMCS) and (MDCS) can be obtained as byproducts of the Rochow synthesis after separation from the main product dimethyldichlorosilane (DMDCS) [K. Schnurrbusch, Ullmanns Encyklopädie der technischen Chemie, Volume 15, Urban & Schwarzenberg-Verlag, pp. 748–749 (1964)]. They are, because of a high DMDCS selectivity, which is desired in the Rochow synthesis, not always available to a sufficient extent. DMCS can be alternatively synthesized by catalytic cracking of organochlorodisilanes, which are present in the residue of the Rochow synthesis [M. Wick, G. Kreis, F. -H. Kreuzer, Ullmanns Encyklopädie der Technischen Chemie, Volume 21, 4th edition, Verlag Chemie, pp. 485–508 (1982)].

A targeted synthesis of DMCS from DMDCS can also be achieved by the reduction of DMDCS with metal hydrides, thus, for example, with LiH [21.06.89-JP-158938], NaH/NaBH$_4$ [02.02.77-JA-010373], CaH$_2$, (TiH$_2$)$_n$ [J. Organomet. Chem. 206 (3), 279–286 (1981)]. In the reduction of DMDCS with LiH in an LiCl/KCl melt at a temperature of from 355° C. to 470° C., a yield of from 8% to 17% of DMCS is obtained [21-06.89-JP-158938]. However, in this reaction procedure there are formed, because of the stoichiometry of the reaction, large amounts of LiCl per unit of DMCS formed. The reduction of DMDCS with NaBH$_4$/NaH in hexamethylphosphoramide as solvent at temperatures of from 40° C. to 80° C. leads to a DMCS yield of 71% [02.02.77-JA010373]. Apart from the use of a carcinogenic hazardous material as solvent, this synthetic route has the disadvantage that large amounts of NaCl are formed per unit of the DMCS formed.

Furthermore, MDCS can be converted into DMCS in a Grignard reaction [K. Schnurrbusch, Ullmanns Encyklopädie der Technischen Chemie, Volume 15, Urban & Schwarzenberg-Verlag, pp. 748–769 (1964)].

The direct synthetic routes described all lead to a high automatic formation of inorganic chlorides which have to be deposited in a landfill or worked up. A need continues to exist for a method by which DMCS and MDCS can be synthesized which avoids metal chloride by-product formation.

SUMMARY OF THE INVENTION

Accordingly one object of the present invention is to provide a method of synthesizing alkylhydrogenchlorosilanes while largely avoiding automatic formation of residual materials which have to be disposed of.

Briefly, this object and other objects of the invention as hereinafter will become more readily apparent can be attained by alkylhydrogenchlorosilanes of formula I prepared by reacting alkylchlorosilanes of formula II with hydrogen in the presence of a catalyst.

DETAILED DESCRIPTION OF THE PREFERRED EMBODIMENTS

The hydrogenation reaction of the present invention is surprising since calculations based on the latest thermodynamic data indicate that the equilibrium of the reaction of DMDCS and hydrogen to give DMCS and HCl lies virtually completely on the side of the starting materials [M. D. Allendorf and C. F. Nelius, J. Phys. Chem. 97, 720–728 (1993)]. For example, the catalytic reaction of DMDCS with hydrogen to give DMCS is carried out over heterogeneous catalysts, generally over conventional hydrogenation catalysts containing at least one transition metal of Group VIII of the Periodic Table of the Elements. Furthermore, the formation of MDCS is also observed here. Trimethylchlorosilane (TMCS) is found as a further useful byproduct.

The invention accordingly provides alkylhydrogenchlorosilanes of formula I $$R_{(4-n-m)}SiCl_nH_m \quad (I),$$

where m and n are each equal to 1 or 2 and m+n≦3 and R is an alkyl group having from 1 to 5 carbon atoms. The alkylhydrogenchlorosilanes of Formula I can be prepared by catalytic reaction of alkylchlorosilanes of formula II $$R_{(4-p)}SiCl_p \quad (II),$$

wherein p is equal to 1 or 2 or 3, with hydrogen.

From the reaction product prepared by the catalytic reaction in this manner, the alkylhydrogenchlorosilanes of formula I can also be isolated in pure form. The pure alkylhydrogenchlorosilanes are preferably obtained by distillative separation from the reaction product.

The alkylhydrogenchlorosilanes of the present invention of formula I can be used in hydrosilylation reactions.

Thus, the alkylhydrogenchlorosilanes of the invention having formula I, in particular the reaction product of the catalytic reaction prepared by the present process and containing the alkylhydrogenchlorosilanes of formula I, can be used, for example, for reaction with an alkene, an alkenyl compound, an alkene, an alkynyl compound and/or organic compounds containing conjugated and/or accumulated double bonds and/or triple bonds. In this way, for example, the reaction of alkylhydrogenchlorosilanes of the invention having formula I with acetylene gives the corresponding vinylalkylchlorosilanes which can, if desired, be separated or further purified by distillation. In such hydrosilylation, it is also possible to use catalysts, appropriately noble metal catalysts, in particular homogeneous catalysts, for example hexachloroplatinic acid [DE-B 12 32 580, U.S. Pat. No. 3,793,358].

The present invention further provides a process for preparing alkylhydrogenchlorosilanes of formula I $$R_{(4-n-m)}SiCl_nH_m \quad (I),$$

wherein m and n are each equal to 1 or 2 and m+n≧3 and R is an alkyl group having from 1 to 5 carbon atoms. Here, alkylchlorosilanes of formula II $$R_{(4-p)}SiCl_p \quad (II),$$

wherein p is equal to 1, 2 or 3, are reacted catalytically with hydrogen and the alkylhydrogenchlorosilanes are isolated from the reaction product.

In general, the process of the invention for preparing alkylhydrogenchlorosilanes of formula I is carried out in such a way that the alkylchlorosilanes of formula II are preferably reacted catalytically in the gas phase with hydrogen. The alkylchlorosilanes of formula II are reacted catalytically with hydrogen at temperatures of from 100° to 600° C. preferably at temperatures of from 400° to 500° C. The alkylchlorosilanes of formula II are also preferably reacted catalytically with hydrogen at pressures of from 1 to 50 bar abs., particularly preferably at pressures of from 5 to 10 bar abs. In the reaction, the molar ratio of hydrogen to alkylchlorosilanes of formula II is normally from 1:1 to 100:1, preferably from 5:1to15:1.

The process of the invention can be carried out continuously or batchwise in a multitube reactor or a fixed-bed reactor with and without recirculation. The catalyst is here appropriately arranged in a fixed catalyst bed. In the reaction, the space velocity (GHSV) i.e. the throughput gas volume of hydrogen based on the catalyst volume used, is appropriately from 10 to 10,000 $h^{-1}$, preferably from 100 to 1,000 $h^{-1}$. If desired, the reaction mixture can be diluted with an inert gas. However, it is also possible to use a fluidized-bed reactor with suitable supported catalysts.

The alkylhydrogenchlorosilanes of formula I prepared by the process of the invention are preferably separated from the reaction product by distillation. The reaction product of the novel catalytic reaction of alkylchlorosilanes of formula II can, apart from the starting materials and the alkylhydrogenchlorosilanes of formula I, also contain other organosilanes, for example trialkylchlorosilanes. Since the main products in the reaction product of the present catalytic reaction of alkylchlorosilanes of formula II are also present in the reaction product of the Rochow synthesis, the distillative workup of the reaction product obtained according to the invention can also be carried out together with the customary distillative workup stages connected downstream of the Rochow synthesis for isolation of dimethyldichlorosilane.

In the process of the invention, the alkylchlorosilanes of formula II are generally reacted with hydrogen over at least one metal of transition Group VIII of the Periodic Table of the Elements (PTE), preferably nickel and/or ruthenium and/or rhodium and/or palladium and/or platinum as catalyst. The catalyst is appropriately applied to a support which preferably contains activated carbon and/or oxides of aluminum and/or of titanium and/or of silicon. To the support is normally applied from 0.01 to 10% by weight, preferably from 0.1 to 6% by weight, more preferably from 0.5 to 5% by weight, of metal of the above-mentioned elements of transition Group VIII of the PTE. For the preparation of the catalyst, the conventional processes for preparing catalysts containing at least one element of Group VIII of the PTE can be carried out. In general, loose-bed catalysts are used in the process of the invention. The catalyst can here be applied to a rod-shaped or tubular or cogwheel-shaped or spherical or chip-shaped support. However, it is also possible to use honeycomb supports or catalyst packs made of individual plates having, for example, a smooth or corrugated or mesh-type structure, or hydrogenation catalysts on other support shapes, for example powder catalysts.

In a preferred embodiment of the process of the invention, dimethyldichlorosilane is reacted catalytically with hydrogen and the dimethylchlorosilane and/or the methyldichlorosilane is isolated from the reaction product. However, the reaction product can also contain other organosilanes, for example trimethylchlorosilane. The process of the invention thus enables the formation of undesired byproducts, which require disposal, to be avoided in a specific manner in the preparation of alkylhydrogenchlorosilanes of formula I.

Having generally described this invention, a further understanding can be obtained by reference to certain specific examples which are provided herein for purposes of illustration only and are not intended to be limiting unless otherwise specified.

EXAMPLE

A silane/$H_2$ mixture produced by saturation of the hydrogen with DMDCS at 30° C. is passed over a Pd/activated carbon catalyst having a metal content of 5% by weight at a GHSV of 470 $h^{-1}$ at 2 bar abs. and 340° C. The DMDCS conversion found and the selectivities with respect to the main products are shown in Table 1.

TABLE 1

| DMDCS conversion % | DMCS sel. % | MDCS sel. % | TMCS sel. % |
| --- | --- | --- | --- |
| 5.3 | 36.1 | 21.6 | 37.3 |

A silane/$H_2$ mixture produced by saturation of the hydrogen with DMDCS at 30° C. was passed over a Pt/activated carbon catalyst having a metal content of 5% by weight at a GHSV of 230 $h^{-1}$ at 10 bar abs. and 400° C. The DMDCS conversion found and the selectivities with respect to the main products are shown in Table 2.

TABLE 2

| DMDCS conversion % | DMCS sel. % | MDCS sel. % | TMCS sel. % |
| --- | --- | --- | --- |
| 3.9 | 40.8 | 52.0 | 5.4 |

EXAMPLE 3

A silane/$H_2$ mixture produced by saturation of the hydrogen with DMDCS at 30° C. was passed over an Ru/$Al_2O_3$ catalyst having a metal content of 1% by weight at a GHSV of 250 $h^{-1}$ at 6 bar abs. and 400° C. The DMDCS conversion found and the selectivities with respect to the main products are shown in Table 3

TABLE 3

| DMDCS conversion % | DMCS sel. % | MDCS sel. % | TMCS sel. % |
| --- | --- | --- | --- |
| 14.8 | 27.2 | 49.5 | 20.0 |

Having now fully described the invention, it will be apparent to one of ordinary skill in the art that many changes and modifications can be made thereto without departing from the spirit or scope of the invention as set forth herein.

What is claimed as new and is desired to be secured by Letters Patent of the United States is:

1. A process for preparing alkylhydrogenchlorosilanes of formula I $$R_{(4-n-m)}SiCl_nH_m \quad (I),$$

wherein m and n are each equal to 1 or 2 and m+n<3 and R is an alkyl group having from 1 to 5 carbon atoms, comprising:

reacting alkylchlorosilanes of formula II $$R_{(4-p)}SiCl_p \qquad (II),$$

wherein p is equal to 1 or 2 or 3, with hydrogen in the presence of a catalyst comprising at least one metal of Group VIII of the Periodic Table of the Elements thereby producing alkylhydrogenchlorosilanes; and subsequently isolating the atkylhydogenchlorosilanes from the reaction product.

2. The process according to claim 1, wherein the alkylhydrogenchlorosilanes of formula I are separated from the reaction product by distillation.

3. The process according to claim 1, wherein the alkylchlorosilanes of formula II are reacted catalytically in the gas phase with hydrogen.

4. The process according to claim 1, wherein the alkylchlorosilanes of formula II are reacted catalytically with hydrogen at temperatures of from 100° to 600° C.

5. The process according to claim 1, wherein the alkylchlorosilanes of formula II are reacted catalytically with hydrogen at pressures of from 1 to 50 bar abs.

6. The process according to claim 1, wherein the alkylchlorosilanes of formula II are reacted with hydrogen over nickel, ruthenium, rhodium, palladium, platinum or combinations thereof as catalyst.

7. The process according to claim 1, wherein the catalyst is a supported catalyst.

8. The process according to claim 7, wherein the amount of catalytically active metal ranges from 0.01 to 10% by wt. on the support.

9. The process according to claim 7, wherein the catalyst is a supported catalyst containing activated carbon, oxides of aluminum, oxides of titanium, oxides of silicon, or combinations thereof.

10. The process according to claim 1, wherein, in the reaction, the molar ratio of hydrogen to alkylchlorosilanes of formula II ranges from 1:1 to 100:1.

11. The process according to claim 1, wherein, in the reaction, the space velocity (GHSV), based on hydrogen, ranges from 10 and 10,000 $h^{-1}$.

12. The process according to claim 1, wherein dimethyldichlorosilane is reacted catalytically with hydrogen and the dimethylchlorosilane, the methyldichlorosilane or combinations thereof are isolated from the reaction product.

13. A method of hydrosilylation, comprising the steps of:
a) reacting alkylchlorosilanes of the formula II $$R_{(4-p)}SiCl_p \qquad (II)$$

wherein p is equal to 1 or 2 or 3, with hydrogen in the presence of a catalyst comprisinq at least one metal of Group VIII of the Periodic Table of the Elements thereby producing alkylhydrogenchlorosilanes; and b) reacting said alkylhydrogenchlorosilanes with an unsaturated hydrocarbon compound.

14. The method according to claim 13, wherein step b) is carried out in the presence of a noble metal catalyst.

15. The method according to claim 14, wherein said noble metal catalyst is hexachloroplatinic acid.

16. The method according to claim 13 wherein said unsaturated hydrocarbon compound is an alkene, an alkenyl an alkynyl compound and/or organic compound containing conjugated and/or accumulated double bonds and/or triple bonds.

* * * * *